(12) United States Patent
Edwards et al.

(10) Patent No.: US 7,368,296 B2
(45) Date of Patent: May 6, 2008

(54) SOLID PHASES OPTIMIZED FOR CHEMILUMINESCENT DETECTION

(75) Inventors: Brooks Edwards, Cambridge, MA (US); Timothy G. Geiser, San Mateo, CA (US); Steven M. Menchen, Fremont, CA (US); Alison L. Sparks, North Andover, MA (US); John C. Voyta, Sudbury, MA (US)

(73) Assignee: Applied Biosystems, Foster City, CA (US)

( * ) Notice: Subject to any disclaimer, the term of this patent is extended or adjusted under 35 U.S.C. 154(b) by 72 days.

(21) Appl. No.: 10/046,730

(22) Filed: Jan. 17, 2002

(65) Prior Publication Data

US 2003/0134286 A1     Jul. 17, 2003

(51) Int. Cl.
*G01N 33/545* (2006.01)
*G01N 33/533* (2006.01)
*C07C 211/62* (2006.01)

(52) U.S. Cl. .................... 436/531; 436/532; 436/530; 436/546; 436/805; 436/823; 564/281

(58) Field of Classification Search ................ 436/531, 436/532, 530, 546, 805, 823; 435/6; 564/281
See application file for complete search history.

(56) References Cited

U.S. PATENT DOCUMENTS

| 2,780,604 | A | 2/1957 | Clarke et al. |
| 3,065,272 | A | 11/1962 | Garner et al. |
| 3,178,396 | A | 4/1965 | Lloyd et al. |

(Continued)

FOREIGN PATENT DOCUMENTS

| DE | 2447611 | 4/1975 |
| EP | 0 294 186 A2 | 12/1988 |
| EP | 0 567 187 A1 | 10/1993 |
| EP | 1 120 422 A1 | 8/2001 |
| WO | WO 92/13018 | 8/1992 |
| WO | WO 96/25667 | 8/1996 |
| WO | WO 99/53319 | 10/1999 |

OTHER PUBLICATIONS

Shizuka, "Excited-State Proton-Transfer Reactions and Proton-Induced Quenching of Aromatic Compounds", Accounts of Chemical Research, 18, 141-147 (1985).
Jones, et al., "p-Vinylbenzyltrialkyl Ammonium Salts in Vinyl Polymerization", Journal of Polymer Science, 25, 201-215 (1957). (Cited as "1958" on p. 19 of the specification).

(Continued)

*Primary Examiner*—Long V. Le
*Assistant Examiner*—Shafiqul Haq
(74) *Attorney, Agent, or Firm*—Merchant & Gould, P.C.; Christopher W. Raimund (57) ABSTRACT

Solid supports for chemiluminescent assays are provided. The solid support includes a plurality of probes covalently or physically attached to the support surface and a chemiluminescent enhancing moiety incorporated onto the surface or into the bulk of the support. The solid support can be a multi-layered support including an upper probe binding layer (e.g., an azlactone polymer layer or porous functional polyamide layer) adjacent to a cationic microgel layer. The azlactone-functional polymer can be a copolymer of dimethylacrylamide and vinylazlactone crosslinked with ethylenediamine. The cationic microgel layer can be a cross-linked quaternary onium salt containing polymer. A method and a kit for conducting chemiluminescent assays using the solid supports is also provided. The kit comprises a dioxetane substrate, a biopolymer probe-enzyme complex, and a solid support. The solid support can be an azlactone functional polymer layer adjacent to a cationic microgel layer; a porous polyamide functional layer adjacent to a cationic microgel layer; or a quaternized azlactone functional polymer layer.

9 Claims, 10 Drawing Sheets

U.S. PATENT DOCUMENTS

| | | | |
|---|---|---|---|
| 3,236,820 | A | 2/1966 | Lloyd et al. |
| 3,770,439 | A | 11/1973 | Taylor |
| 3,898,088 | A | 8/1975 | Cohen et al. |
| 3,958,995 | A | 5/1976 | Campbell et al. |
| 4,308,335 | A | 12/1981 | Yamamoto et al. |
| 4,322,489 | A | 3/1982 | Land et al. |
| 4,340,522 | A | 7/1982 | Bronstein-Bonte et al. |
| 4,424,326 | A | 1/1984 | Land et al. |
| 4,503,138 | A | 3/1985 | Bronstein-Bonte et al. |
| 4,563,411 | A | 1/1986 | Bronstein-Bonte |
| 4,737,560 | A | 4/1988 | Heilmann et al. |
| 4,871,824 | A | 10/1989 | Heilmann et al. |
| 4,981,933 | A | 1/1991 | Fazio et al. |
| 5,200,471 | A | 4/1993 | Coleman et al. |
| 5,336,596 | A | 8/1994 | Bronstein et al. |
| 5,336,742 | A | 8/1994 | Heilmann et al. |
| 5,547,836 | A | 8/1996 | Bronstein et al. |
| 5,593,828 | A | 1/1997 | Bronstein et al. |
| 5,672,514 | A | 9/1997 | Tsuchiya et al. |
| 5,705,357 | A | 1/1998 | Kissel et al. |
| 5,827,650 | A | 10/1998 | Bronstein et al. |
| 5,849,495 | A | 12/1998 | Bronstein et al. |
| 5,981,185 | A * | 11/1999 | Matson et al. ............... 435/6 |
| 6,162,610 | A | 12/2000 | Bronstein et al. |
| 2001/0012537 | A1* | 8/2001 | Anderson et al. ............ 427/2.1 |

OTHER PUBLICATIONS

Dahlberg, et al., "Electrostatic Catalysis of Proton-Transfer Reactions: Hydrogen Exchange in Chloroform and Ionization of 2-Nitropropane", J. Am. Chem. Soc, 105, 5387-5390 (1983).

Rosenthal, et al., "Acid-Base Equilibria in Concentrated Salt Solutions. IV. Some Bases of Various Charge Types in Dilute Acid Solutions", The Journal of Physical Chemistry, 69, 5, 1588-1595 (1965).

Bardsley, et al., "Synthesis and Oxidation of Aminolkyl-onium Compounds by Pig Kidney Diamine Oxidase", Biochem, J., 122, 557-567 (1971).

Ing, et al., "CCCXII. —A Modification of the Gabriel Synthesis of Amines", J. Chem. Soc., 2348-2351 (1926).

Sasaki, et al., "Convenient Synthesis of Some Purine 8,5'-Imino Cyclonucleosides", J. Org. Chem., 43, 12, 2320-2324 (1978).

Khan, Kinetic Evidence for the Occurence of a Stepwise Mechanism in Hydrazinolysis of Phthalimide, J. Org. Chem., 60, 4536-4541 (1995).

Motawia, et al., "A Convenient Route to 3'-Amino-3'-Deoxythymidine", Synthesis, 384-387 (1989).

Durette, et al., "Bacterial Cell Wall Constituents. II. Synthesis of O-( N-Acetyl-β-Muramyl-L-Alanyl-D-Isoglutamine)—(1-4) - N-Acetyl-D- Glucosamine", Tetrahedron Letters, 42, 4013-4016 (1979).

* cited by examiner

SOLID PHASES OPTIMIZED FOR CHEMILUMINESCENT DETECTION

BACKGROUND OF THE INVENTION

1. Field of the Invention

The present invention relates generally to solid phases for use in connection with biological assays. More specifically, the invention pertains to solid materials which can be used for chemiluminescent assays based on 1,2-dioxetanes which can be triggered by enzymes and enzyme conjugates in ligand-binding pairs to emit light.

2. Background of the Technology

Increasingly, blotting assays employing chemiluminescent detection have become a popular modality for the detection of biomolecules such as proteins and nucleic acids. Conventionally, such assays are conducted by isolating a sample of the analyte on a membrane, exposing that membrane to an antibody-agent or nucleic acid probe agent complex, wherein the agent causes a composition to be added to undergo chemiluminescence. In its most widely practiced form, this type of blotting assay employs an enzyme or enzyme conjugate as the agent causing a compound which can decompose to release light to undergo that decomposition, thereby giving chemiluminescence. Among the most effective compounds for this purpose are 1,2-dioxetanes. These structures, if stabilized with an adamantyl group or similar stabilizing group, or with a derivatized adamantyl group, can be protected with an enzyme-labile group to form an enzyme cleavable substrate. When cleaved by a suitable enzyme, the substrate forms an unstable anion, which then decomposes to release light. For example, using an enzyme, the chemiluminescent compound is a substrate, and among dioxetane substrates, AMPPD disodium 3-(4-methoxy-spiro[1,2-dioxetane-3,2'-tricyclo[3.3.1.1$^{3,7}$]de-can]-4-yl) phenyl phosphate is widely used. Structurally related compounds, wherein the adamantyl group is substituted with various electron-active groups, convert the adamantyl moiety from a mere stabilizing agent to one which actively influences dioxetane decomposition. Among these, the chlorine-substituted compound, or CSPD, has been demonstrated to be particularly effective. A wide variety of other compounds, bearing other enzyme-labile protective groups, such as sugar, acetate and other ether and ester moieties are known and effective.

Various protocols are used in blotting assays. In a Western or Southern Blotting assay, for example, proteins or nucleic acids are purified and transferred to membrane supports. The membranes are typically nitrocellulose, polyamide (e.g. nylon), or polyvinylidene fluoride (PVDF). This transferred material (analyte) is incubated with at least one antibody specific for the compound being sought (e.g., specific protein or nucleic acid). In a Western Blotting assay, the antibody can be complexed with an enzyme, or, alternatively, a second antibody complexed with an enzyme can be added following a washing step. In the case of AMPPD and CSPD, the binder (antibody or DNA/RNA probe) is conjugated with an alkaline phosphatase enzyme. Subsequent to washing, the blot is incubated with the chemiluminescent substrate. Release of chemiluminescence is confirmation of the presence of the suspected compound or target analyte.

In Southern blotting procedures, a nucleic acid sample is blotted onto a membrane following gel electrophoresis separation. Hybridizations are performed with enzyme labeled nucleic acid probes (labeled directly or indirectly via biotin-avidin or antibody-antigen bridge) containing base sequence complementary to regions specific for the target sample. Again, subsequent to washing, the blot is incubated with the chemiluminescent substrate and the subsequent release of light signal provides confirmation of the presence of the suspected nucleic acid sequence.

These blotting formats present certain problems in connection with the membrane supports typically employed. For instance, the chemical content of the membrane surface, to which the chemiluminescent substrate is exposed, has a tendency to quench or promote quenching of the emitted light, thus reducing the intensity of the chemiluminescent signal. Further, the membranes used have significant lot-to-lot variations, due to current production processes. As a result, it is difficult both to standardize the process and to provide for automatic data acquisition. Among specific problems encountered are low signal levels, very high non-specific backgrounds, and membrane-initiated decomposition of chemiluminescent substrates, such as AMPPD and CSPD.

When dealing with dioxetane substrates such as AMPPD, it is important to note that these compounds have very low intensities of chemiluminescence in aqueous or protic environments. This is believed to be due principally to proton transfer quenching reactions, or dipole-dipole interactions which tend to promote dark reactions of the excited state ultimately produced by enzyme cleavage. Proton transfer reactions are extremely well known in organic chemistry, and can easily compete with light emission during the lifetime of the excited state, which is several orders of magnitude longer. See, for example, *Shizuka,* "Accounts of Chemical Research", 18, 141-147 (1985). This can be confirmed by the fact that the chemiluminescent efficiency of AMPPD in aqueous buffers is approximately only $10^{-6}$, but improves, in the presence of a hydrophobic medium, by approximately $10^4$.

In addition to the above-noted problems, conventional blotting assays continue to leave certain goals unmet. Of particular importance is the inability to quantify the amounts of individual nucleic acid fragments, or proteins, identified in blotting applications. Currently, blotting assays are qualitative in nature, confirming only the presence or absence of a particular component (nucleic acid or protein). Frequently, a component will be present to varying extents in multiple analytes, but diagnosis of a disease or particular molecular biological condition depends on the relative number of component species in the analyte. Current blotting techniques do not permit adequate quantitative discrimination on this basis.

Another shortcoming of prior art blotting assays is the resolution obtainable with conventional solid support materials. It would be desirable to provide material compositions which would enable the quantitative detection of sharply resolved signal generating regions, corresponding to a bound component in the absence of or greatly diminished greatly diminished background signal. Such a material compositions would be suitable for automated data acquisition. As an example, scanning charged-coupled devices can be employed in reading complex information such as spatially localized DNA or RNA sequences on a surface. Such automation would enable a higher efficiency of error-free data acquisition. Current blotting assays conducted on surfaces utilizing chemiluminescent compounds such as dioxetanes do not provide the necessary sharp resolution of high intensity signal producing regions or loci with sufficiently diminished background to permit automated data acquisition. More importantly, these blotting methods and materials are wholly insufficient for application to high-density molecular (nucleic acid or protein) microarrays where more quantitative individual target quantitation is desirable.

Various solutions to the aforementioned problems have been proposed. For example, cationic layers comprising onium salt containing polymers have been proposed for use as membranes in chemiluminescence assays. These membranes have been used to reduce the background noise and to improve the sensitivity and reliability of chemiluminescent assays. See, for example, U.S. Pat. Nos. 5,336,596; 5,593,828; 5,827,650 and 5,849,495.

A need still exists, however, for solid phases which can be used for chemiluminescent assays based on enzyme-triggerable dioxetanes which yield improved signal collection from higher feature density signal generating regions. These solid phases would enable a more quantitative analysis of spatially localized analytes on/in the surface of the material. Such materials would allow for improved chemiluminescent signal detection particularly in high density microarray analysis formats.

SUMMARY OF THE INVENTION

In a first aspect of the invention, solid phases for enhancing chemiluminescent emissions are provided. In one embodiment of the invention, the solid phase comprises a chemiluminescent enhancing material and a biopolymer probe such as a hybridizing probe physically or covalently attached to a surface of the solid phase. The probe itself can comprise a naturally occurring biopolymer, a synthetic analog of a biopolymer, or a combination of naturally occurring and synthetic segments. The molecular probe can be covalently attached to the solid phase by reacting a functional group on the probe with a functional group on the surface of the solid phase. The chemiluminescent enhancing material can be incorporated into the bulk of the solid phase as, for example, a component of a hydrogel, or coated on or covalently attached to the surface of the solid phase. The chemiluminescent enhancing compound can be a quaternary onium compound. When coated on the surface of the solid phase, the quaternary onium compound can be a quaternary onium polymer. According to a further embodiment of the invention, the probes and/or the chemiluminescent enhancing compound can be present on the surface of the solid phase in spatially defined regions. The solid phase having spatially defined regions of biopolymer probes and/or chemiluminescent enhancing compound can be used as a support for microarray based chemiluminescent assays.

According to a second aspect of the invention, a solid phase comprising a layered composite of a probe binding material and an underlying quantum yield enhancing material is provided. The layered composite can include, for example, a functional polymer layer adjacent to a layer comprising a cationic microgel layer. The functional polymer can be a copolymer of dimethylacrylamide and vinylazlactone crosslinked with ethylenediamine whereas the cationic microgel layer can comprise a cross-linked quaternary onium salt containing polymer. In a further embodiment, the solid phase can include a copolymer of dimethylacrylamide and vinylazlactone crosslinked with ethylenediamine and the enhancing material can comprise a polymeric quaternary onium salt. The polymeric support material can comprise a porous polyamide membrane containing surface functional groups capable of binding probes for nucleic acid targets and the enhancing material can comprise a polymeric quaternary onuim salt.

According to a third aspect of the invention, a method of conducting a chemiluminescent assay as set forth above is provided wherein the solid support comprises either a quantum yield enhancing material such as porous polyamide that has been chemically modified with a quaternized onium functionality, or a quaternized onium azlactone functional polymer. According to a preferred embodiment of the invention, the quaternized azlactone functional polymer comprises azlactone repeating units quaternized with aminofunctional quaternary onium compound or quaternized benzyl halide repeating units.

According to a fourth aspect of the invention, a method of conducting a chemiluminescent assay using a solid phase as set forth above is provided. The method includes steps of: contacting the solid phase with an analyte; treating the analyte contacted with the material composition with an antibody enzyme complex and/or a nucleic acid probe-enzyme complex; incubating the enzyme complex treated analyte with an enzyme-cleavable 1,2-dioxetane, wherein the enzyme-cleavable 1,2-dioxetane can be cleaved by an enzyme to yield a chemiluminescent dioxetane reporter molecule; and measuring the degree of chemiluminescence obtained.

According to a fifth aspect of the invention, a kit for conducting chemiluminescent assays to determine the presence or absence of a component of an analyte is provided. The kit includes: a dioxetane substrate bearing an enzyme-labile protecting group which, when cleaved, yields a chemiluminescent reporter molecule; an antibody-enzyme complex and/or a nucleic acid probe-enzyme complex, wherein the antibody or nucleic acid probe is specific for the component being assayed, and wherein the enzyme is capable of cleaving the enzyme-labile protecting group; and a solid phase as set forth above.

BRIEF DESCRIPTION OF THE DRAWINGS

The invention will be described with reference to the accompanying figures, wherein.

DETAILED DESCRIPTION OF THE INVENTION

The present invention enables efficient chemiluminescent enhancement of surfaces. According to one aspect of the invention, a chemiluminescent enhancing moiety, such as a positively charged onium moiety, is incorporated onto a surface or into the bulk of a solid phase. The enhancing moiety can be uniformly distributed across the surface or within the solid phase. Alternatively, the enhancing moiety can be localized or spotted within specific discrete areas or regions of the support. A localized presence of enhancing moieties can allow the light produced from the enzymatic hydrolysis of a 1,2-dioxetane substrate to be enhanced locally at the site of a binding reaction while no enhancement will be produced elsewhere on the surface.

Application of the enhancing moiety to the surface of the support can occur through the coating or deposition of, for example, a solution containing the enhancing material directly onto the desired regions of the membrane surface. Alternatively, the enhancing moiety can be applied to the support surface through covalent attachment of the enhancing moiety to the desired areas on the membrane surface through suitable attachment chemistry. An enhancing component can also be blended into the polymeric material comprising the solid support prior to forming the polymeric material into a membrane. In this manner, the enhancing moiety can be uniformly distributed in the solid support.

Both the uniform surface/bulk modification and the selective formation of discrete enhancing areas on a surface can be applied to assays of biological component surfaces, particularly in the construction of miniaturized arrays for genetic and proteomic analysis.

In another embodiment of the invention, a chemiluminescent enhancing solid support for chemiluminescent assays is provided. The solid support according to the invention can be a multi-layer structure comprising a probe binding layer (e.g., an azlactone functional polymer layer or a porous polyamide functional polymer layer) and a cationic microgel layer. The multi-layer structure can be used by itself as a membrane or, alternatively, the multi-layer structure may be provided on a backing material. When provided on a backing material, conventional membranes for use in assays (e.g., polyamide, PVDF and nitrocellulose) can be used as backing materials for the multi-layer structure of the invention. However, any material that is inert with respect to the components of the assay can also be used as the backing material for the multi-layer structure of the invention. By using a multi-layered structure according to the invention, chemiluminescence detection can be enhanced and the radial diffusion of the deprotected dioxetane reporter molecule from spatially localized analyte can be limited.

The probes according to the invention can be naturally occurring biopolymers, synthetic analogs of biopolymers and biopolymers comprising naturally occurring and synthetic segments. For example, the probes can be nucleic acid, antibody or avidin probes (including avidin variants).

Figure 1:
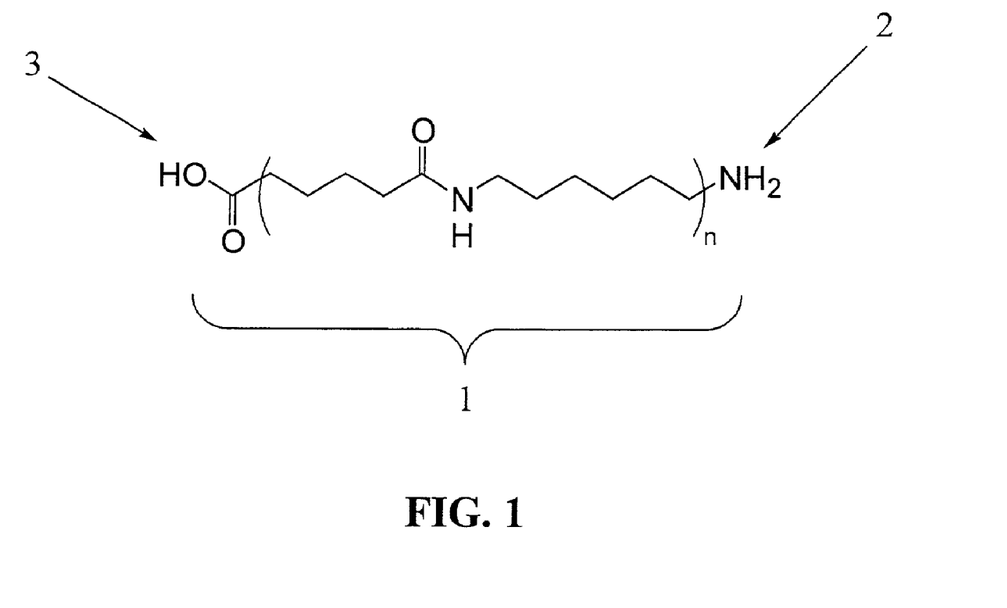
FIG. 1 shows the general structure of a polyamide which can be used to prepare a solid support according to the invention.

An example of a functional polymer that can be used as a probe binding material for a solid support according to the invention is shown in FIG. 1. The polymer shown in FIG. 1 (which is a copolymer prepared from hexanediamine and adipic acid commonly referred to as nylon 66) has a polyamide backbone 1. This polymer contains both amino groups 2 and carboxylate groups 3 which can serve as potential probe binding functionalities. The probe binding functionalities in polyamides are intrinsic to the structure of the polymer and result from the monomers and techniques used to synthesize the polymer. Although polyamides are shown, any polymer having intrinsic probe binding functionalities can be used as a probe binding material.

Polymers that contain no intrinsic binding functionalities can also be used as probe binding layers according to the invention. These polymers can be modified through various well known chemical techniques after synthesis of the polymer. In addition, other chemical modification techniques can be used to modify the surface of the solid support after manufacture of the support.

Figure 2A:
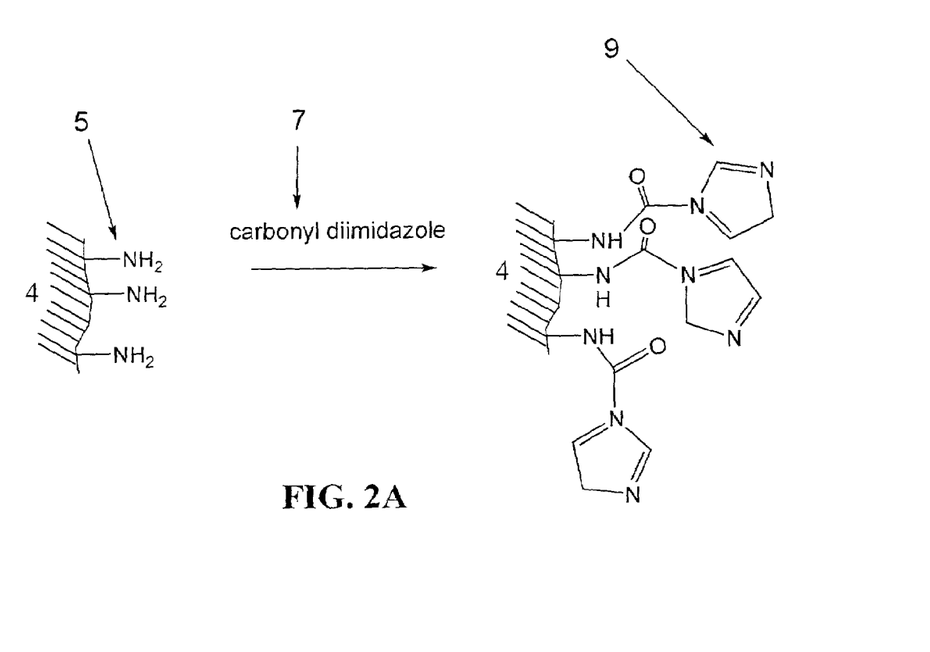
FIGS. 2A and 2B illustrate two possible methods of activating functional surfaces so that probes containing nucleophilic groups can be covalently bound to the functional surface.
Figure 2B:
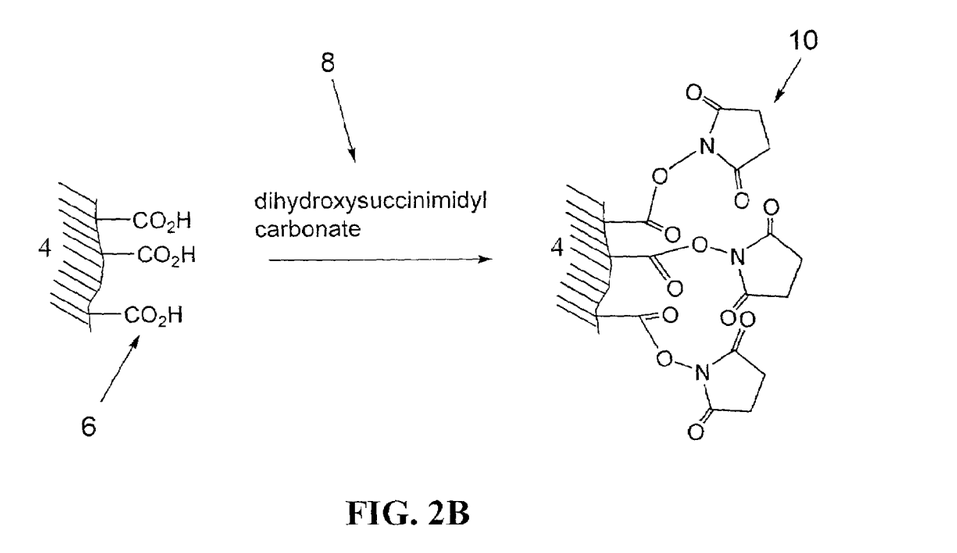

Potential methods for activating functional membrane surfaces so they can be bound with probes that can hybridize nucleic acid targets are shown in FIGS. 2A and 2B. The membrane shown in FIGS. 2A and 2B can be a polyamide membrane prepared from a polymer similar to that shown in FIG. 1. As shown, the membrane 4 has accessible amino groups 5 and/or carboxylate groups 6 on its surface. If the probe has a nucleophilic functional group, such as amino groups, then the membrane surface functionalities can be converted to electrophilic groups in order to from covalent linkages with the probes. As shown in FIG. 2A, for example, amino groups 5 can be converted into electrophilic imidazole ureas 9 by reaction with carbonyl diimidazole 7. Other reagents that can convert amine groups into electrophilic groups include, but are not limited to, dihydroxysuccinimidyl carbonate, phosgene, and phenylchloroformate. As shown in FIG. 2B, carboxylate groups 6 can be converted into electrophilic hydroxysuccinimidyl esters 10 by reaction with dihydroxysuccinimidyl carbonate 8. Other reagents that can convert carboxylate groups into electrophilic groups include, but are not limited to, carbodiimides, oxalyl chloride, and carbonyl diimidazole. With the use of electrophilic probes, the intrinsic amine groups 5 on the support surface can be used to form covalent bonds with the probes.

Various known methods can be used to convert the membrane surface groups into anionic or cationic groups and these functionalities used to bind probes. In addition, a membrane surface which has activated amine or carboxylate groups can be reacted with, for example, polyethyleneimine to yield a high density of amine groups on the membrane surface. Subsequent reaction of the aminated surface with a cyclic anhydride, such as succinic anhydride, will yield a carboxylated membrane surface with much higher functional group density compared to the original polyamide surface. These carboxylates can then be activated and conjugated with probes as set forth above.

Figure 3:
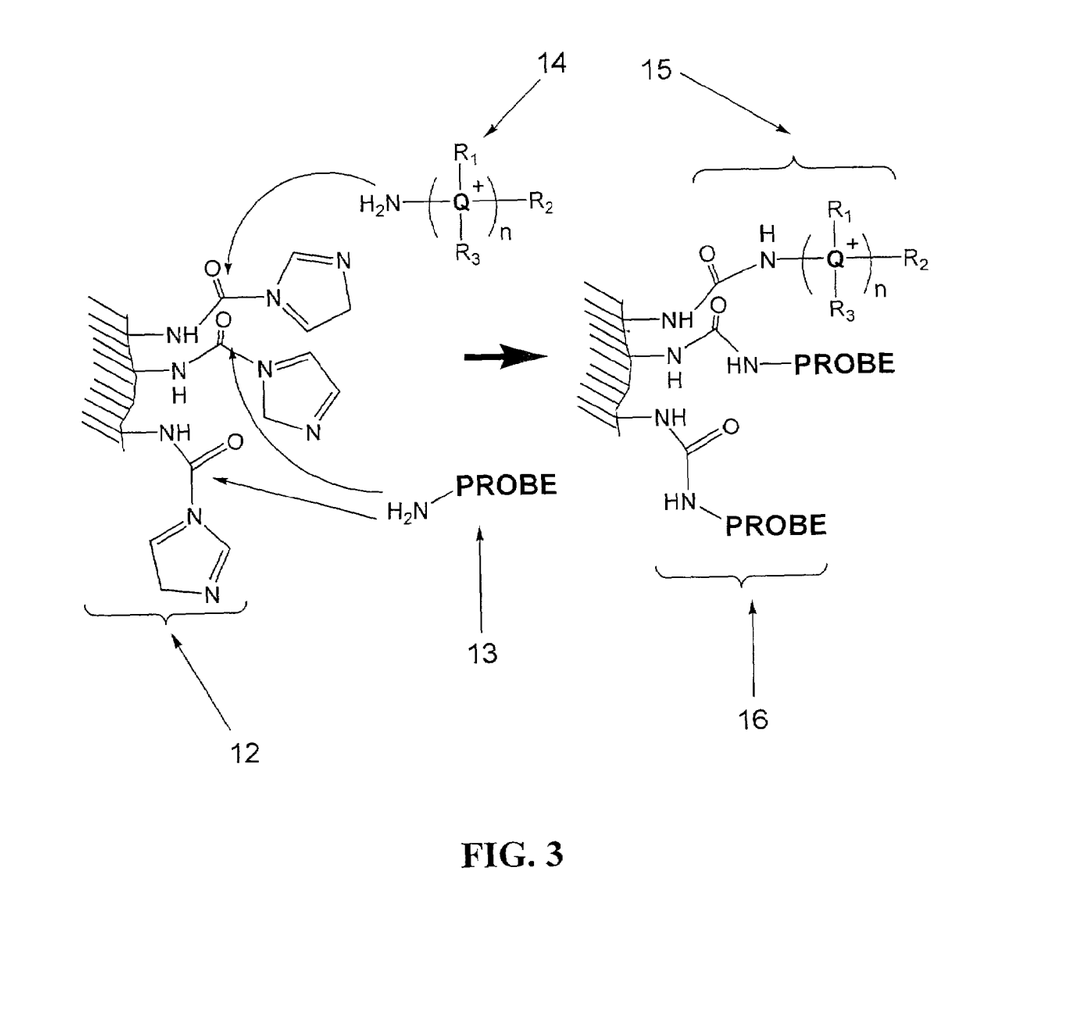
FIG. 3 shows the reaction of an amino linked onium quaternary compound and an amino linked probe with functional groups on a solid support surface.

FIG. 3 shows a method for covalently binding nucleic acid probes 13 containing nucleophilic functional groups such as amines to surfaces modified with electrophilic imidazole urea groups 12 to yield covalent urea linkages 16. As shown in FIG. 3, the active surface of the membrane can also be used to locally bind chemiluminescent enhancing moieties 14. As shown in FIG. 3, chemiluminescent enhancing moiety 14 contains a functional group (e.g., an amine) capable of forming a urea covalent linkage 15 with a functional group (e.g., an imidazole urea group) on the membrane surface. Using this strategy, probe and chemiluminescent enhancer can be co-spotted on the membrane surface, thereby limiting the chemiluminescent signal enhancement to the area where the probe is spotted on the membrane.

Figure 4:
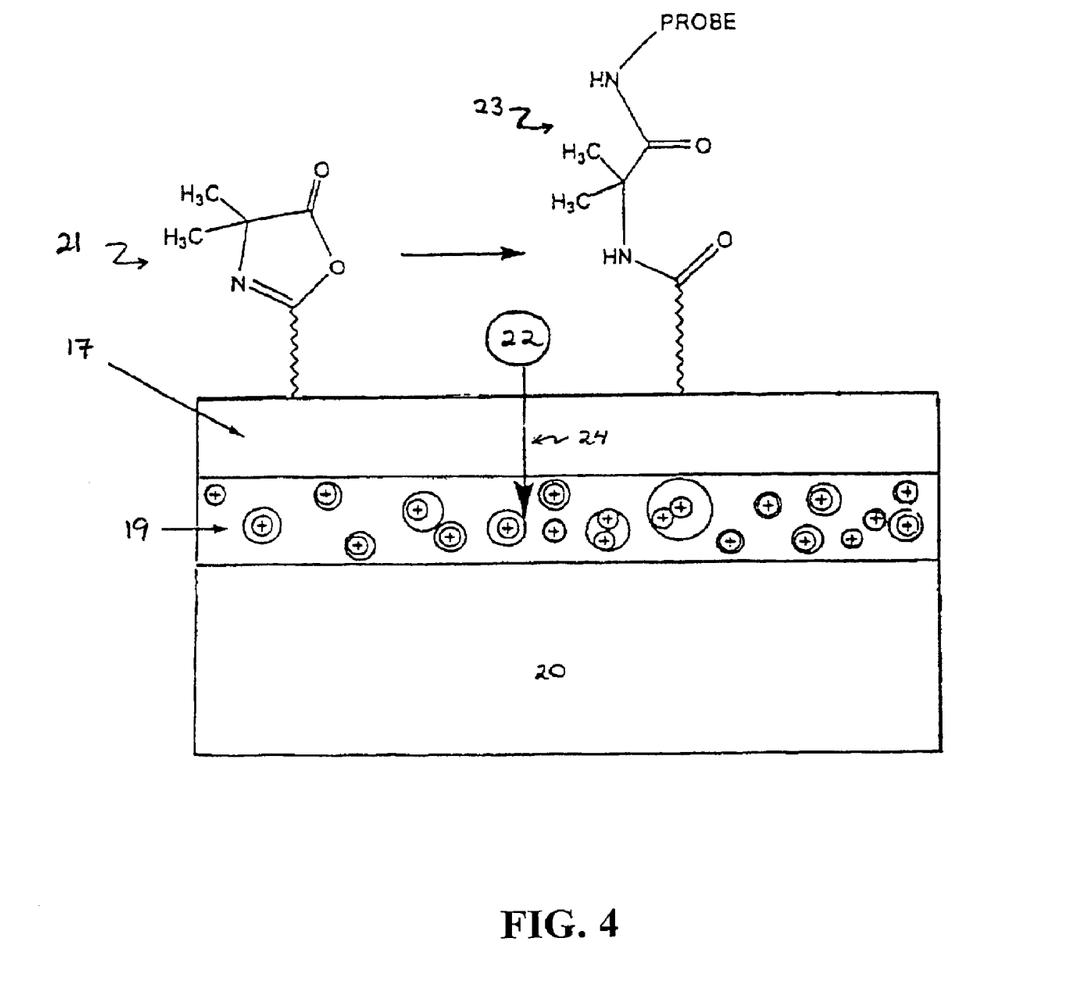
FIG. 4 shows a multi-layered solid phase according to an embodiment of the invention.

An example of a multi-layer solid support according to the invention is shown in FIG. 4 wherein an azlactone functional layer 17 is shown adjacent to a cationic microgel layer 19. As can be seen from FIG. 4, the azlactone functional layer comprises azlactone functional groups 21 on a surface thereof. The azlactone functional groups 21 can be reacted with functional groups on a target or probe to covalently bond the probe to the solid support surface. Covalent attachment can be accomplished using known techniques. In FIG. 4, an amino-functional probe is shown reacted with an azlactone functional group resulting in a covalently bonded probe 23. In FIG. 4, the multi-layered solid support is shown disposed over a backing material comprising an oriented polymer layer 20. The oriented polymer layer 20 can be used to increase the density of binding sites on the solid support.

According to the invention, a solid support for chemiluminescent assays having high feature density can be made by a method comprising steps of: applying a solid support to a shrinkable backing material; applying a chemiluminescent quantum yield enhancing material to an exposed surface of the solid support; applying a plurality of probes for a biopolymer target to an exposed surface of the solid support; and shrinking the backing material. The quantum yield enhancing material and/or the probes can be applied to the exposed surface of the solid support in a plurality of spaced, discrete regions. Further, the quantum yield enhancing material and/or the probes can be covalently attached to the exposed surface of the solid support. The solid support can comprise an azlactone functional layer or a polyamide functional layer. Further, the solid support can comprise an azlactone functional layer or a porous polyamide functional layer adjacent to a layer comprising a cationic microgel.

The shrinkable backing material can comprise an oriented polymer layer which relaxes or shrinks upon heating. Various methods of increasing the feature density of solid supports are disclosed in PCT Publication WO 99/53319, which is hereby incorporated by reference in its entirety. Any of these methods can be used to increase feature density according to the invention.

The microgel layer 19 can be disposed onto functional polymer layer 17 either before or after binding the functional polymer layer with a probe. The functional polymer layer having bound probes can then be treated with an analyte containing a component being assayed.

In use, dioxetane reporter molecules (e.g. anions) 22 generated at or near the solid support surface by reaction with a spatially localized analyte-enzyme complex can diffuse through the azlactone functional layer or porous polyamide functional layer 10 in the direction represented by arrow 24 and become sequestered in the underlying cationic microgel containing layer 19. The hydrophilic azlactone functional layer 17 can be lightly cross-linked so that it will swell when contacted with the aqueous assay solution. This can facilitate diffusion of the dioxetane reporter molecules through the azlactone functional layer.

The azlactone functional polymer layer is preferably a copolymer of dimethylacrylamide and vinylazlactone which has been lightly crosslinked to form a hydrogel. In a preferred embodiment of the invention, cross-linking results from reacting a finite number of the azlactone pendant moieties with ethylenediamine. Reaction can be carried out in a suitable solvent such as isopropyl alcohol (IPA). The resulting azlactone functional layer therefore comprises a crosslinked, water-soluble polymer that swells but does not dissolve on rehydration. It is thus properly defined as a hydrogel in this condition. Such a hydrogel will allow the diffusion of lower molecular weight species such as the dioxetane anion while preventing the diffusion of higher molecular weight biological components of the assay.

Suitable azlactone-functional polymers are disclosed in U.S. Pat. Nos. 4,737,560; 4,871,824 and 5,336,742. As set forth in the aforementioned patents, the azlactone functional polymers comprise a repeating unit having the formula I:

wherein $R_1$ is H or $CH_3$, $R_2$ and $R_3$ independently can be an alkyl group having 1 to 14 carbon atoms, a cycloalkyl group having 3 to 14 carbon atoms, an aryl group having 5 to 12 ring atoms, an arenyl group having 6 to 26 carbon and 0 to 3 S, N, and nonperoxidic O heteroatoms, or $R_2$ and $R_3$ taken together with the carbon to which they are joined can form a carbocyclic ring containing 4 to 12 ring atoms, and n is an integer 0 or 1.

In the multi-layer support according to the present invention, a layer comprising a cationic microgel is provided adjacent to the azlactone functional or porous polyamide functional layer. This layer can be, for example, a cationic microgel layer or a hydrogel comprising a cationic microgel component. The cationic microgel layer acts as a receiving layer to sequester chemiluminescent reporter molecules (e.g., 1,2-dioxetane phenolate anions) produced by enzymatic action in or near the surface of the adjacent azlactone functional polymer layer or porous polyamide functional layer.

According to a further embodiment of the invention, the cationic microgel layer comprises a polymeric onium salt, particularly a quaternary onium salt, based on phosphonium, sulfonium and/or ammonium moieties. Polymers of this type are known in art. Suitable polymers, for example, have been used as mordant layers in photographic processes. See, for example, U.S. Pat. Nos. 3,958,995 and 5,827,650. The cationic microgels can be in the form of crosslinked quaternary onium (e.g., ammonium, sulfonium or phosphonium) salt-containing latices.

In one embodiment, the quaternary onium polymers according to the invention can comprise a repeating unit having the general formula (II):

In the above formula, each of $R_1$, $R_2$ and $R_3$ can be a straight or branched chain unsubstituted alkyl group having from 1 to 20 carbon atoms, inclusive, e.g., methyl, ethyl, n-butyl, t-butyl, pentyl, neopentyl, hexyl, or the like; a straight or branched chain alkyl group having from 1 to 20 carbon atoms, inclusive, substituted with one or more hydroxy, alkoxy, aryloxy, amino or substituted amino, amido, or ureido; or fluoroalkane or fluoroaryl, groups, an unsubstituted monocycloalkyl group having from 3 to 12 carbon ring carbon atoms, inclusive, a substituted monocycloalkyl group having from 3 to 12 ring carbon atoms, inclusive, substituted with one or more alkyl, alkoxy or fused benzo groups (e.g., methylcyclohexyl or 1,2,3,4-tetrahydronaphthyl), a polycycloalkyl group having 2 or more fused rings, each having from 5 to 12 carbon atoms, inclusive, unsubstituted or substituted with one or more alkyl, alkoxy or aryl groups (e.g., 1-adamantyl or 3-phenyl-1-adamantyl), an aryl, alkaryl or aralkyl group having at least one ring and from 6 to 20 carbon atoms in toto, unsubstituted or substituted with one or more alkyl, aryl, fluorine or hydroxy groups (e.g., phenyl, naphthyl, pentafluorophenyl, ethylphenyl, benzyl, hydroxybenzyl, or phenylbenzyl); at least two of $R_1$, $R_2$ and $R_3$, together with the quaternary nitrogen atom to which they are bonded, can form a saturated or unsaturated, unsubstituted or substituted nitrogen-containing, nitrogen and oxygen-containing or nitrogen and sulfur-containing ring having from 3 to 5 carbon atoms, inclusive, and 1 to 3 heteroatoms, inclusive, and which may be benzoannulated (e.g., 1-pyridinium, 1-(3-alkyl or aralkyl)imidazolium, alkyl morpholinium, alkylpiperidinium, dialkylpiperazinium, acylalkylpiperazinium, benzoxazolium, benzothiazolium or benzamidizolium. The symbol M in formula II can be N or P.

The symbol $X^-$ in formula II represents a counter ion which can include, alone or in combination, moieties such as a halide, i.e., fluoride, chloride, bromide or iodide, a sulfate, an alkylsulfonate (e.g., methylsulfonate), an arylsulfonate (e.g., p-toluenesulfonate), a substituted arylsulfonate (e.g., anilinonaphthylenesulfonate or diphenylanthracenesulfonate), a perchlorate, an alkanoate (e.g., acetate), an arylcarboxylate (e.g., fluorescein or fluorescein derivatives), a benzoheterocyclic arylcarboxylate (e.g., 7-diethylamino-4-cyanocoumarin-3-carboxylate). Furthermore, organic dianions such as p-terephthalate may also be represented by $X^-$. The counter ion $X^-$ is preferably selected to improve solubility and to change ionic strength as desired, and is preferably halogen, a sulfate, or a sulfonate.

The symbol n in formula II is a positive integer. According to one embodiment of the invention, n represents a number such that the molecular weight of the poly(vinylbenzyl quaternary ammonium salts) will range from about 800 to about 200,000 (weight average), and preferably from about 20,000 to about 70,000, as determined by intrinsic viscosity or LALLS techniques.

Methods for the preparation of the ammonium polymers (i.e., where M in formula II above is nitrogen), related copolymers and the related starting materials are disclosed in Jones et al., Journal of Polymer Science, 25, 201 1957; in U.S. Pat. Nos. 2,780,604; 3,178,396; 3,770,439; 4,308,335; 4,340,522; 4,424,326 and in German Offenlegunsschrift 2,447,611.

The corresponding phosphonium polymers (i.e., where M in formula II above is phosphorous) are described in U.S. Pat. Nos. 3,236,820 and 3,065,272.

Copolymers containing 2 or more different pendant onium groups may also be used according to the invention.

Methods for preparing the quaternary onium polymers are also disclosed in the above referenced U.S. Patents. For example, the quaternary onium polymers can be prepared by free radical polymerization of the appropriate precursor monomers or by exhaustive alkylation of the corresponding tertiary amines with polyvinylbenzyl chloride, or copolymers containing a pendant benzyl chloride function.

The quaternary onium polymers can also be used as a solid support without an overlying azlactone or polyamide layer according to the invention. When used in this manner, the support can comprise a quaternary onium polymer having a repeating unit represented by the following general formula (III):

(III)

wherein n is as defined above and wherein each R group is an n-pentyl group. The use of n-pentyl groups on an ammonium center has been found to provide a desired degree of hydrophobicity to the support surface for conducting bioassays, particularly in a micro-array format. The quaternary onium polymer can be crosslinked according to the invention to improve the durability of the support.

The quaternary onium polymers according to the invention may be used as the membrane alone or as a coating on other supports. The supports can be used to lend stability to the polymer. The support should be suitable for use in the physical manipulations of the assay and be inert with respect to the elements of the assay. Plates or beads comprising glass or inert polymers, and the like, may be acceptable supports for overcoating with the polymer of the invention. Alternatively, these quaternary polymers and copolymers can be coated as a single layer from an admixture with polyamide, PVDF, nitrocellulose and other polymeric binders. In one embodiment, membranes typically used in blotting assays, such as polyamide membranes, PVDF and in particular, nitrocellulose membranes can be used as the support and/or functional polymer and overcoated with the quaternary onium polymers of the invention.

To overcoat a support, the polymer solution can be deposited on the support (e.g., membrane) and rolled across the surface of the support (e.g., with rubber tubing) to provide a uniform coating. Alternative methods of coating including (but not limited to) dipping, spraying and the like may also be employed. After coating, the overcoated support can then be dried in an oven (e.g., at 50-100° C. for about 15 minutes).

Figure 5:
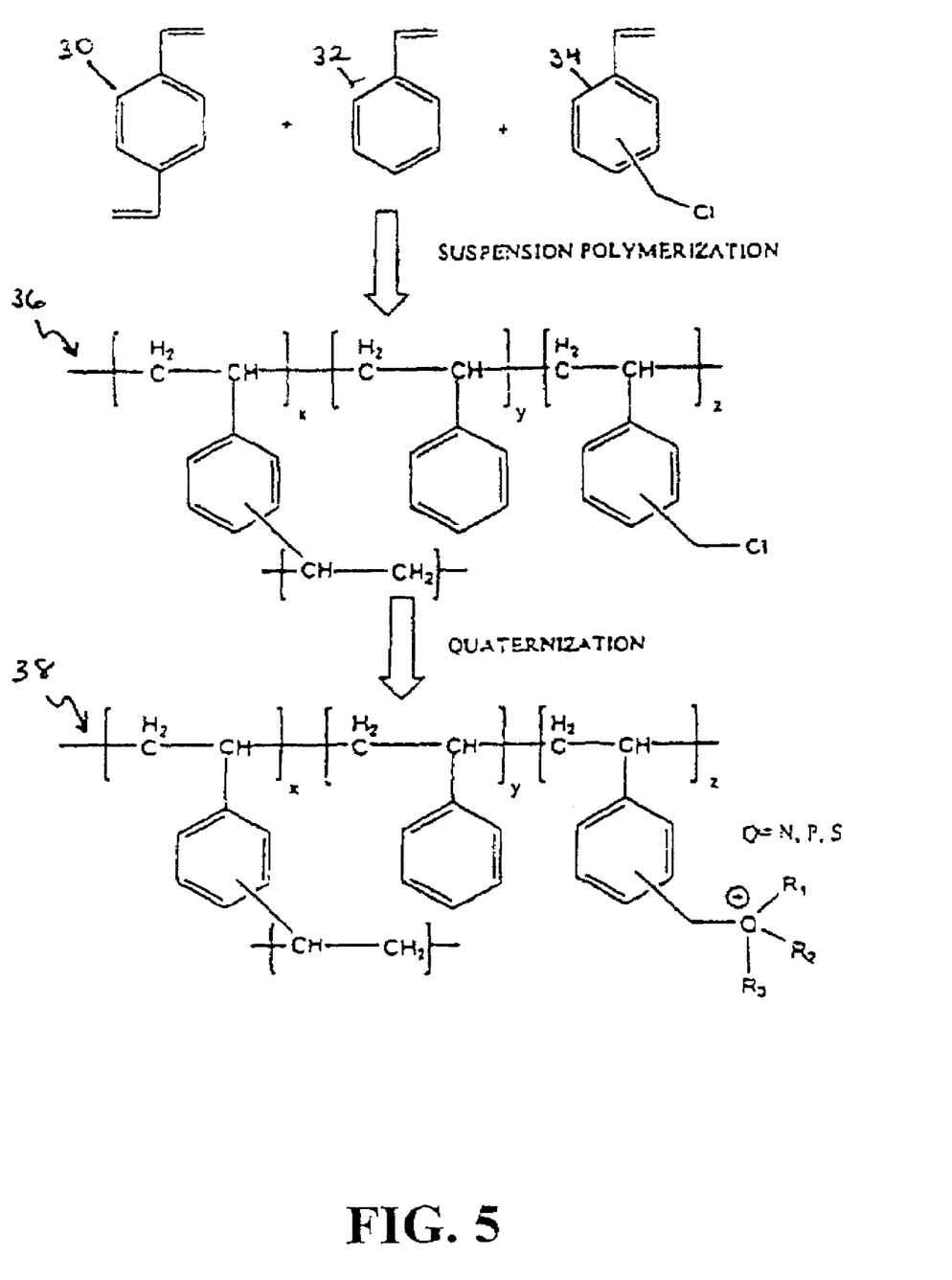
FIG. 5 illustrates a method of synthesizing a cationic microgel.

FIG. 5 illustrates a method that can be used for synthesizing a cationic microgel according to the invention. As can be seen from FIG. 5, the quaternary onium polymers can be synthesized from a monomer mixture. This monomer mixture can contain a variable mole percentage of a bis-ethylenically unsaturated crosslinking moiety such as divinyl benzene 30. Additional monomers in the feed may be styrene 32 or other hydrophobic co-monomers, and vinylbenzyl chloride 34.

As shown in FIG. 5, the quaternary onium monomers can be polymerized via suspension polymerization to form a cross-linked polymer 36. The resulting polymer 36 can then be subject to quaternization by reaction of the vinylbenzyl chloride derived repeating unit with a variety of tertiary amines using known techniques to form the quaternized polymer 38.

When emulsion polymerization in water is utilized to synthesize the polymers, the crosslinked polymer 36 is obtained as a crosslinked latex. Upon quaternization, the polymeric latex becomes hydrophilic and therefore swells but does not dissolve in aqueous solution. The quaternized polymer 38 can therefore be considered a hydrogel or microgel.

The individual vinylbenzyl quaternary onium salt monomers used to prepare the poly(vinylbenzyl quaternary ammonium salts) of formula II above can also be co-polymerized with other ethylenically unsaturated monomers having no quaternary ammonium functionality. Polymers of this type are disclosed in U.S. Pat. Nos. 4,322,489; 4,340,522; 4,424,326; 4,503,138; 4,563,411; and 3,898,088. These copolymers can also be used as cationic microgel layers according to the invention.

The positively charged quaternary onium microgel layer immediately adjacent to the azlactone functional polymer layer according to the invention can enhance the diffusion of chemiluminescent reporter molecules through the azlactone functional layer. In particular, coulombic forces and hydrophobic-hydrophobic interactive forces can steer the diffusion of a dioxetane anion generated by cleaving a dioxetane substrate through the swollen azlactone functional hydrogel layer or porous polyamide functional polymer layer to the adjacent enhancing layer. In this manner, the intensity of the chemiluminescent signal can be increased. Further, the lateral diffusion of the phenolate anion can be reduced and, consequently, the resolution of the assay can be enhanced.

The properties of the cationic microgel layer can be tailored by varying the mole fractions of the monomers in the feed and by varying the substituents on the tertiary amine or phosphine used in the quaternization reaction.

The cationic microgel layer according to the invention can be formed by coating the quaternary polymer in an aqueous solution on a surface. The surface can be a substrate which is intended to become part of the support or, alternatively, the layer can be removed from the substrate. In a preferred embodiment, the quaternary polymer solution further comprises a film-forming polymer, which can be any water soluble or water compatible polymer that the cationic microgel layer to be coated from an aqueous solution (e.g., water or water and a water-miscible co-solvent). The film-forming polymer may also be chosen to optimize other parameters such as layer flexibility and adhesion to adjacent layers in the solid support. The film forming polymers may be chosen from a wide variety of materials. Suitable film forming materials include, but are not limited to, agarose gelatin, polyvinyl alcohol, polyvinyl pyridine and salts thereof, PEOX, polyvinylpyrrolidone, or polyethylene oxide, and mixtures thereof.

According to a preferred embodiment of the invention, an azlactone-containing polymer (e.g., an azlactone-dimethylacrylamide copolymer) may be reacted with a quaternary onium compound having an azlactone reactive functional group (e.g., an amino-alkyl or amino-aralkyl quaternary salts). Reaction can be conducted before or after crosslinking the polymer (e.g., with ethylenediamine) but is preferably conducted before cross-linking. For example, amino functionalities on an amino-alkyl or amino-aralkyl quaternary salts can can be reacted with the azlactone functional groups in the azlactone functional polymer to form a crosslinked quaternary hydrogel.

Figure 6:
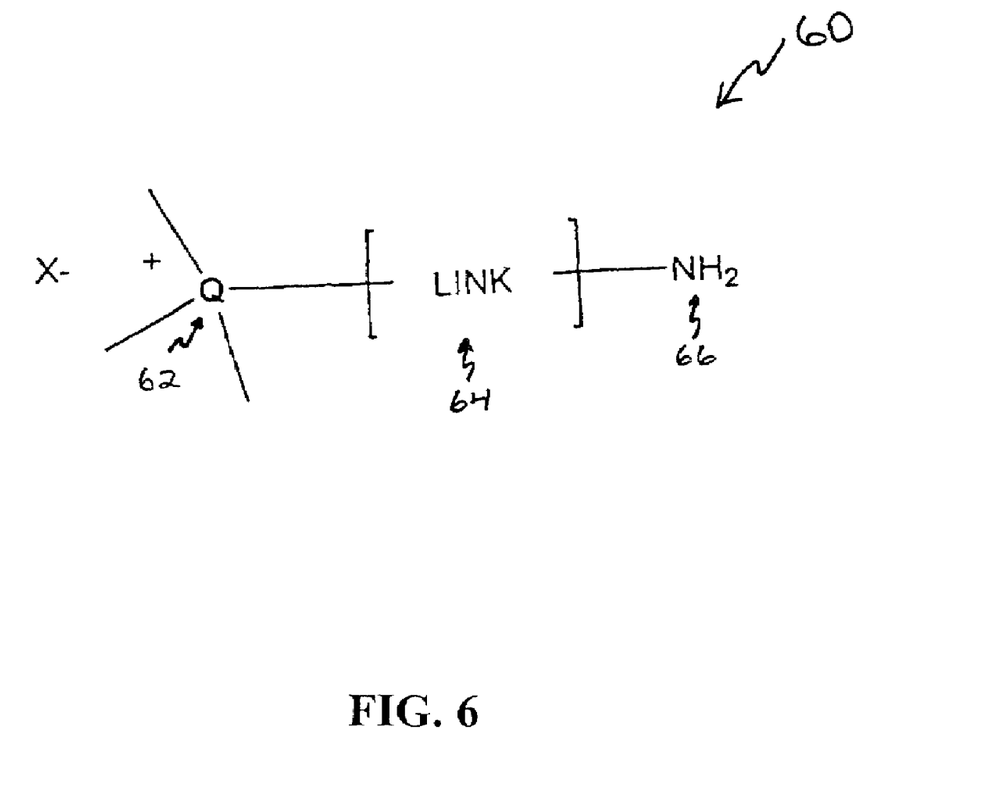
FIG. 6 shows a general formula for an amino linked onium quaternary compound according to the invention.

Suitable amino functional quaternary salts that can be used to quaternized an azlactone functional polymer are defined by the general formula of FIG. 6. As shown in FIG. 6, the amino functional quaternary onium compound 60 comprises a positively charged onium moiety 62 attached by a linker arm 64 to an amino functional group 66. Although a primary amino group is shown, a secondary amino group can also be used. The onium moiety 62, which is represented in FIG. 6 by "Q", may be a nitrogen or a phosphorus.

Figure 7:
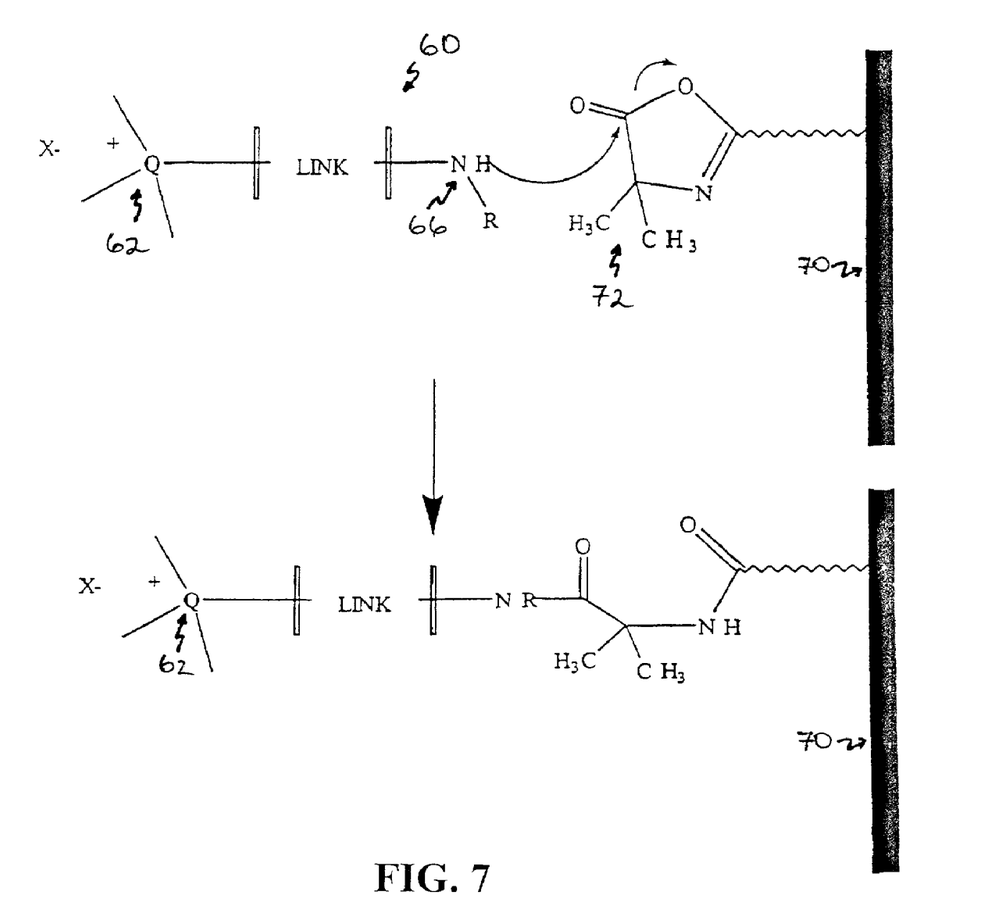
FIG. 7 shows the reaction of an amino linked onium quaternary compound according to FIG. 6 with an azlactone functionality in an azlactone functional polymer.

FIG. 7 illustrates a process of reacting an amino linked onium quaternary compound 10 as defined in FIG. 6 with the surface of a solid support 70. As illustrated in FIG. 7, the amino functional group 66 of the quaternary onium compound 60 can be reacted with an electrophilic azlactone functionality 72 on the surface of a solid support 70 via the amino functional group 66. In this manner, the covalent immobilization of the onium moiety 62 on the support surface 70 can be achieved. The substituent R on the amino group in FIG. 7 can be a hydrogen, an alkyl, a benzyl or an aryl group.

Various amino functional quaternary onium compounds can be employed according to the invention. These amino onium quaternary compounds can be synthesized using known techniques.

Figure 8A:
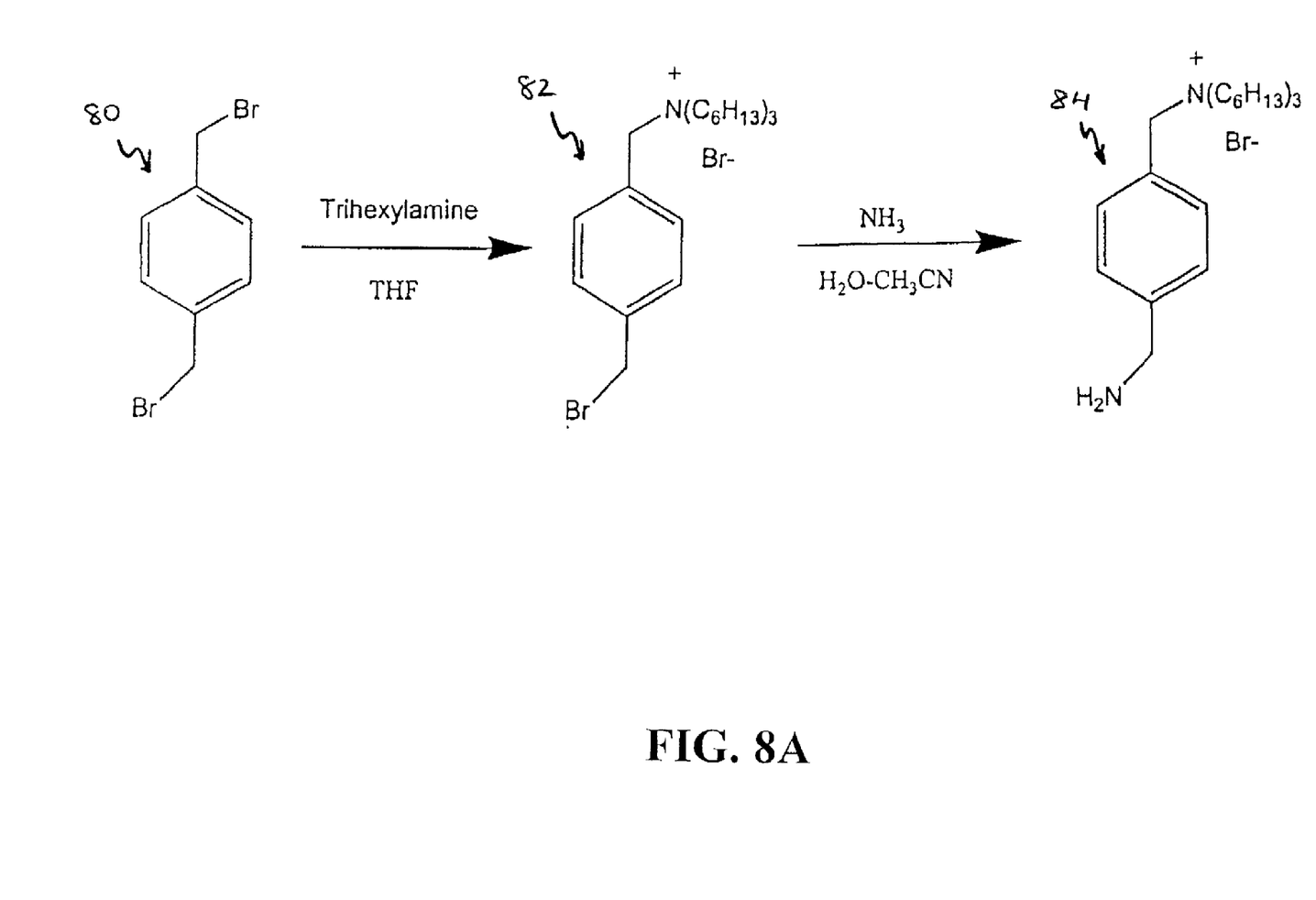
FIG. 8A illustrates the synthesis of an amino linked onium quaternary compound with a p-xylene linker.

A first example of the synthesis of an amino onium quaternary compound is illustrated in FIG. 8A. The amino onium quaternary compound shown in FIG. 8A utilizes a para-xylene unit for the linker moiety. In a first step in the synthesis of the amino onium quaternary compound according to FIG. 8A, dibromo-p-xylene 80 is reacted with a tertiary amine (e.g., trihexyl amine). Although a tertiary amine is shown in FIG. 8A, a phosphine can also be used. As shown in FIG. 8A, the reaction can be conducted in a precipitating solvent such as THF to give the mono-quaternary salt 82. By using a precipitating solvent, the mono-quaternary salt precipitates out of solution as it is formed and is thus easily isolated.

In a second step, the mono-quaternary salt (i.e., a quaternary bromide) 82 is reacted with excess ammonia in aqueous acetonitrile to yield the amino-quaternary onium salt 84.

The use of an aromatic linker as set forth in FIG. 8A can provide a rigid-rod effect at the surface of the solid support due to the rigidity of the p-xylene linker moiety. Additionally, the presence of the aromatic linker on the support surface can be used to provide intermediates and products that have UV absorption for reaction monitoring by TLC.

The linker moiety of the amino-quaternary onium salt according to the invention may also be an aliphatic chain. When the linker is an aliphatic chain, a method as set forth in FIG. 8B may be used to synthesize the amino functional quaternary onium compound.

Figure 8B:
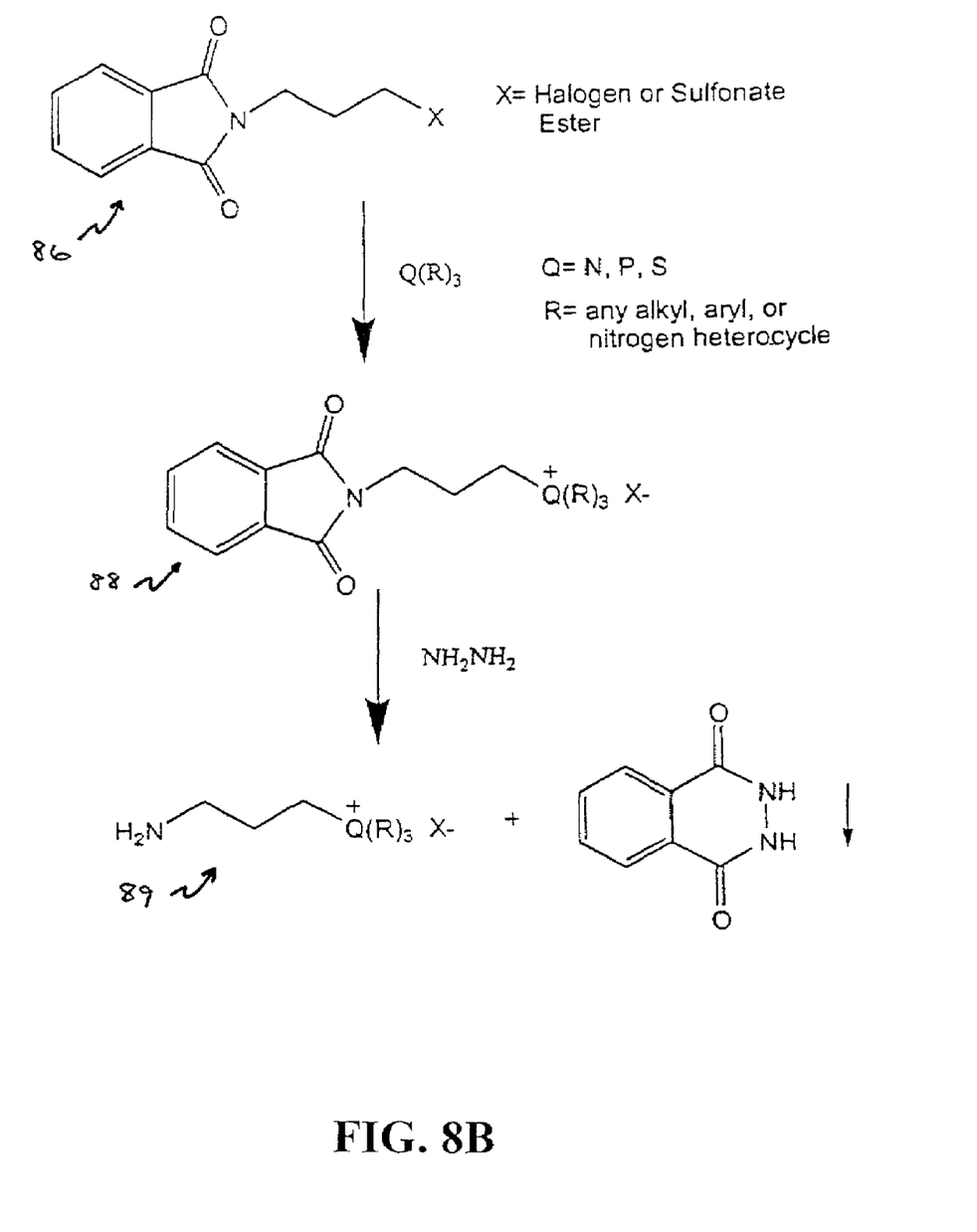
FIG. 8B shows the synthesis of an amino linked onium quaternary compound having an n-alkyl linker.

In the method shown in FIG. 8B, an N-(n-bromoalkyl) phthalimide (i.e., bromopropylphthalimide) 86 is used to alkylate a tertiary or heterocyclic amine or a tertiary phosphine. The insolubility of the phthalhydrazide 88 produced during deprotection of the phthalimide to the terminal amino group via an Ing-Manske procedure can be used to obtain a relatively pure amino-linked onium quaternary compound 89 without using elaborate purification procedures. This procedure is known in the art as set forth in the following references: J. Am. Chem. Soc., 105, 5387 (1983); J. Phys. Chem., 69, 1588 (1965); Biochem. J., 122, 557 (1971); J. Chem. Soc., 2348 (1926); J. Org. Chem., 43, 2320 (1978); J. Org. Chem., 60, 4536 (1995), Synthesis, 384 (1989); Tetrahedron Lett., 4013 (1979).

Figure 9:
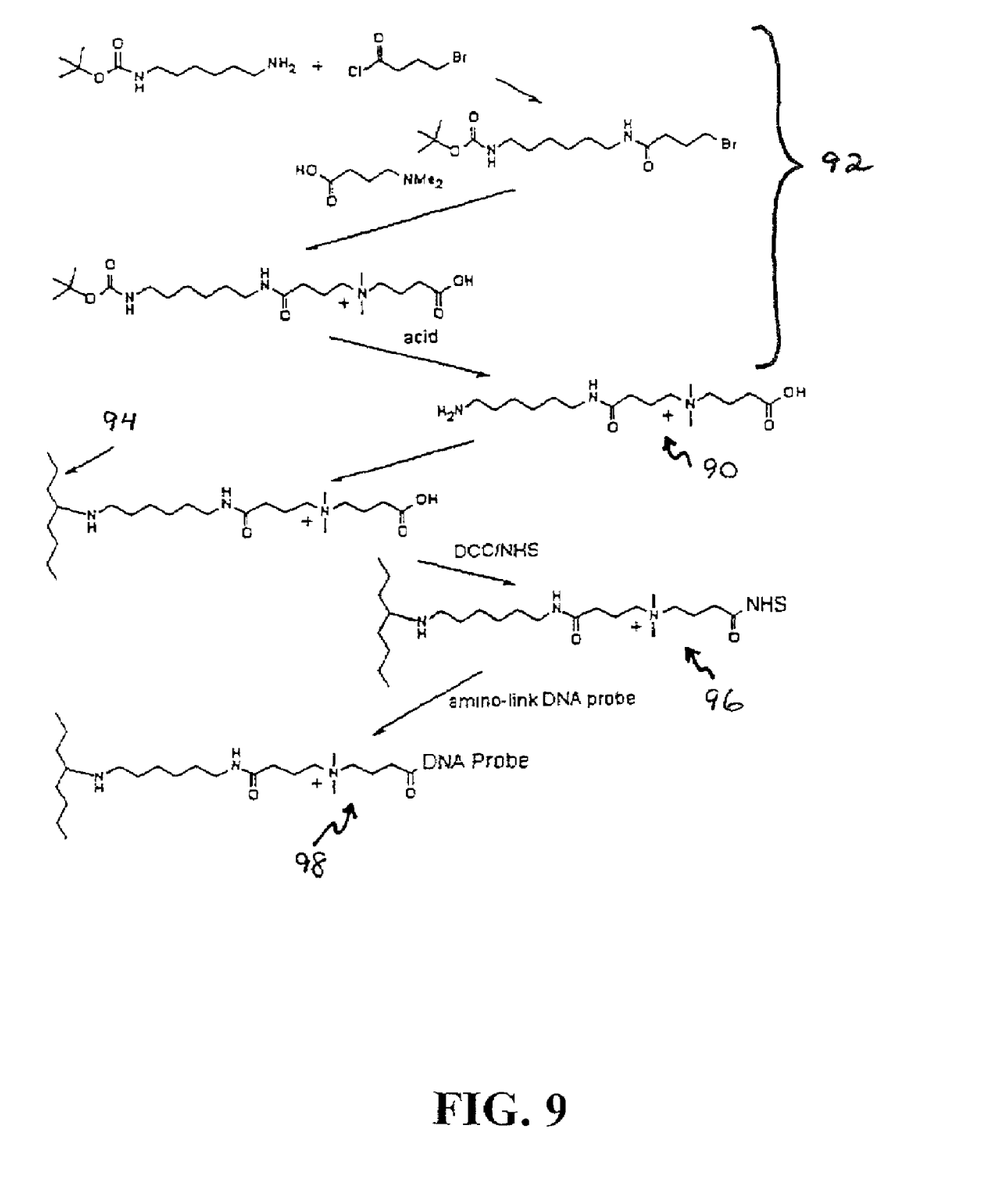
FIG. 9 illustrates a method of covalently bonding an onium species having a latent functionality to an electrophilic surface, activating the latent functionality, and attaching a DNA probe.

In a further embodiment of the invention, an onium species comprising a latent functionality can be covalently bonded onto a solid support surface (e.g., a functionalized polyamide surface or an azlactone functional surface). The latent functionality can then be activated for direct attachment of a probe. An example of this embodiment of the invention is illustrated in FIG. 9 wherein an amino linked onium enhancing moiety having a latent functionality 90 is synthesized in a series of steps 92 and covalently bonded to a support surface 94. The support surface 94 can be an azlactone functional surface or a functionalized polyamide surface. The amino linked onium enhancing moiety having a latent functionality 90 can then be activated 96 and the DNA probe covalently bonded thereto to form the covalently bonded DNA probe 98.

The enhancing material having a latent functionality as set forth above can be locally spotted or uniformly applied onto the solid support surface 94. When the enhancing material having a latent functionality is uniformly applied onto the solid support surface 94, activation can be done either locally, or globally followed by local probe spotting. For example, activation of the latent functionality can be done locally (through some spotting technique) and the oligo probe bathed over the entire surface. In this manner, the oligo probe becomes covalently bonded to the support surface in those area defined by the activation. In addition, activation can be done globally or uniformly across the surface and the oligo probe can be spotted locally for defined anchoring.

The above chemistry can be applied to azlactone modified surfaces in two ways. First, the surface can be modified uniformly. In this manner, the entire surface of the support can be optimized for chemiluminescence detection. This method could be applied to beads or membranes of various materials (e.g., glass surfaces, silicon surfaces, polymeric materials, etc.).

Second, a biological reagent (e.g., a protein or amine-containing nucleic acid probe) and an amino-linked onium quat may be simultaneously or sequentially immobilized in the same spot. In this method, the relative stoichiometry and the reaction rates of the surface azlactone with the amino-linked biological agent and the amino-linked onium quat can influence the resulting product. The resulting localized positive onium center can be utilized to specifically enhance a chemiluminescent signal produced by a bound biological reagent. In this manner, any background chemiluminescence produced from enzyme deprotected 1,2-dioxetane that has diffused from the location of the enzyme or from emission of light from enzyme non-specifically bound to non-spot areas would not be enhanced, thus increasing the apparent resolution of the assay.

Alternatively, an azlactone functional polymer or copolymer having quaternary onium functional groups incorporated therein can be used as a solid support. A polymer of this type is disclosed in U.S. Pat. No. 4,981,933. The resulting quaternized copolymer can be used alone as a solid support (i.e., single layer) or as the cationic microgel layer in a multi-layer solid support according to the invention after crosslinking with a limited quantity of diamine. The single-layer or multi-layer support can also be provided on a backing material.

The quaternized azlactone functional polymer can be used alone as a solid support. In a preferred embodiment of the invention, however, the quaternized azlactone functional polymer is used as the cationic microgel layer of a multi-layer solid support comprising an azlactone functional or functionalized porous polyamide layer adjacent to the quaternized azlactone functional polymer layer. In a further preferred embodiment, the azlactone functional polymer that is quaternized to form the cationic microgel layer is the same base polymer that is used in the upper azlactone functional polymer layer, wherein the azlactone functional polymer in the upper layer is crosslinked with a diamine.

As noted above, the single- and multi-layer solid supports according to the invention may be used alone as a membrane or, alternatively, may be provided on a backing material. The backing material can be used to lend stability to the multi-layer structure as well as to facilitate physical manipulations of the assay. The backing material for the solid support will preferably be made of a material that is inert with respect to the elements of the assay. Glass, polymeric materials, beads and the like, can be used as backing materials for the multi-layer polymer support of the invention. The backing materials can be in the form of plates, sheets, films or beads. In a preferred embodiment of the invention, a conventional assay membrane material (e.g., polyamide, PVDF or nitrocellulose) can be employed as the backing material for the multi-layer structure of the invention.

According to the invention, a target probe may be attached to the exposed azlactone or functionalized polyamide surface of the multi-layer structure. For example, a probe having a functional group (e.g., an amino group) that is reactive with functional groups (e.g., azlactone groups) present on the surface of the multi-layer structure may be covalently bonded to the surface of the solid support.

According to a further preferred embodiment of the invention, an azlactone ring or other reactive functionality in the polyamide or azlactone functional layer and/or in the cationic microgel layer can be used to immobilize or co-immobilize a fluorescent moiety such as a fluorescein or rhodamine dye. For example, the amino functional group on an aminoalkyl fluorescein or rhodamine dye can be reacted with azlactone functional groups on the support surface. These fluorescent moieties can, in some applications, serve as a localized covalently-bonded energy transfer acceptor for the electromagnetic radiation released by the 1,2-dioxetane.

The solid supports according to the invention have various advantages over prior art supports. According to one aspect of the invention, a diffusion limiting and chemiluminescence enhancing solid support can be created in the coating or manufacturing stage. Therefore, the end user is not required to treat the support surface with any ancillary chemiluminescence enhancing reagent or to spot the probes with chemiluminescence enhancing reagent in the spotting solution (i.e, with an amino-alkyl or -aralkyl quaternary onium salt). Further, using the multi-layer structure of the invention, the need to reactivate any azlactone ring opening product for reaction with amino-link terminated probes can be obviated.

The solid supports according to the invention can be made by known techniques. For example, if the multi-layer structure is used as a membrane, the individual layers can be cast on a surface in succession and then removed from the casting surface to form the membrane. When the solid support is formed on a substrate, any known coating technique can be employed. For example, a solution of the polymer can be deposited on the substrate and spread across the surface thereof (e.g., with a roller or other spreading means) to provide a uniform coating over the entire substrate. Alternative methods of coating such as dipping, spraying and the like, however, may also be employed.

The solid supports according to the invention are not limited to any particular form. For example, the solid supports according to the invention can be in the form of sheets or beads or any other form known in the art.

The solid supports according to the invention can be used in assays wherein the presence or absence of one or more components of an analyte is ascertained. Chemiluminescent assays according to the invention can comprise steps of: contacting the analyte with the solid support; treating the analyte on the solid support with an antibody enzyme complex and/or a nucleic acid probe-enzyme complex;

incubating the enzyme complex treated analyte with a chemiluminescent substrate (e.g., an enzyme-cleavable 1,2-dioxetane); and measuring the degree of chemiluminescence obtained. Further, the solid support surface can be washed after the treating step and before the incubating step.

According to a preferred embodiment of the invention, the reporter molecule (e.g., phenolate anion) is tailored to have as short a half life ($t_{1/2}$) as possible while still allowing sufficient time diffusion through the azlactone functional layer or porous polyamide functional layer to the adjacent cationic microgel enhancing layer. In this manner, the radial diffusion of the reporter molecule can be limited. Radial diffusion of the reporter molecule can result in false positive signals or loss of quantitation precision due to signal cross-talk, particularly when using a high density array where adjacent test sites are located in close proximity. Reduction of the half-life of the reporter molecule reduces the extent of diffusion of the active dioxetane reporter molecule to these adjacent test sites. According to the invention, the half-life of the reporter molecule preferably ranges from several seconds to several minutes (e.g., from about 2 seconds to about 60 minutes) depending on the thickness of the azlactone layer and the diffusion constant of the reporter molecule in the azlactone layer.

The solid supports according to the invention can also be provided in a kit for conducting chemiluminescent assays to determine the presence and amount of a component of an analyte. The assay kits according to the invention can include a dioxetane substrate bearing an enzyme-labile protecting group which, when cleaved, yields a chemiluminescent reporter molecule; an antibody-enzyme complex and/or a nucleic acid probe-enzyme complex, wherein the antibody or nucleic acid probe is specific for the component being assayed, and wherein the enzyme is capable of cleaving the enzyme-labile protecting group; and a solid support according to the invention.

From the foregoing, it will be appreciated that although specific embodiments of the invention have been described herein for purposes of illustration, various modifications may be made without deviating from the spirit and scope of the invention.

What is claimed is:

1. A method of modifying the surface of a solid support to enhance the quantum yield of chemiluminescent emissions, the method comprising:
    reacting a functional group on a chemiluminescent enhancing compound with functional groups on the surface of the solid support to covalently attach the chemiluminescent enhancing compound to the surface of the solid support; and
    attaching a plurality of immobilized probes for a biopolymer target to the surface of the solid support,
    wherein the chemiluminescent enhancing compound has the general formula:

wherein Q is N or P; LINK is a divalent linker moiety; $R_1$, $R_2$ and $R_3$ are, independently, an alkyl group, an aryl group or a nitrogen heterocycle; R is hydrogen, an alkyl group, or an aryl group; and $X^-$ is a counterion; and wherein the step of covalently attaching the chemiluminescent enhancing compound to the surface of the solid support comprises reacting the amino group on the quaternary onium compound with the functional groups on the surface of the solid support.

2. The method of claim 1, wherein the functional groups on the solid support surface comprise azlactone groups.

3. The method of claim 1, wherein the solid support composes a polyamide, the method further comprising:
    activating the functional groups on the polyamide surface by reacting amine or carboxylate groups on the polyamide surface with an activating agent.

4. The method of claim 3, wherein the activating agent is reacted with amine groups and the activating agent is selected from the group consisting of: carbonyl diimidazole; dihydroxysuccinimidyl carbonate; phosgene; and phenylchloroformate.

5. The method of claim 3, wherein the activating agent is reacted with carboxylate groups and the activating agent is selected from the group consisting of: dihydroxysuccinimidyl carbonate; carbodiimides; oxalyl chloride; and carbonyl diimidazole.

6. The method of claim 1, wherein the chemiluminescent enhancing compound comprises a functional group linked to an onium moiety, the method further comprising activating the functional group and reacting with a functional group on a probe for a biopolymer target to covalently attach the probe to the chemiluminescent enhancing compound.

7. A solid support for chemiluminescent assays comprising:
    a support having a surface;
    a chemiluminescent quantum yield enhancing moiety covalently attached to the surface of the support, the chemiluminescent quantum yield enhancing moiety having the general formula:

wherein Q is N or P; LINK is a divalent linker moiety; $R_1$, $R_2$ and $R_3$ are, independently, an alkyl group, an aryl group or a nitrogen heterocycle; R is hydrogen, an alkyl group, or an aryl group; and $X^-$ is a counterion; and
    a plurality of immobilized probes for a biopolymer target, wherein the probes are covalently, ionically or physically attached to the surface of the support.

8. The solid support of claim 7, wherein the chemiluminescent quantum yield enhancing moiety is present in spatially defined regions on the surface of the planar support.

9. A kit for conducting chemiluminescent assays to determine the presence or absence of an analyte, comprising:
    a) a dioxetane substrate bearing an enzyme-labile protecting group which, when cleaved, yields a chemiluminescent reporter molecule; and
    b) an antibody-enzyme complex and/or a nucleic acid probe-enzyme complex, wherein the antibody or nucleic acid probe is specific for the analyte, and wherein the enzyme is capable of cleaving the enzyme-labile protecting group; and
    c) the solid support of claim 7.

* * * * *